United States Patent

Bradberry et al.

Patent Number: 5,412,957
Date of Patent: May 9, 1995

[54] KNIT THERAPEUTIC STOCKING WITH ANTI-SLIP FEATURE

[75] Inventors: Laylon Bradberry; John Pendergrass, both of Seneca, S.C.

[73] Assignee: The Kendall Company, Mansfield, Mass.

[21] Appl. No.: 138,110

[22] Filed: Oct. 20, 1993

[51] Int. Cl.$^6$ ............................................. D04B 11/00
[52] U.S. Cl. .................................... 66/178 A; 2/239; 602/63
[58] Field of Search .................. 602/76, 75, 63, 62; 2/239, 161.8; 66/185, 202, 178 R, 186, 197, 198, 199; 61/178 R, 186, 197, 198, 199

[56] References Cited

U.S. PATENT DOCUMENTS

| | | | |
|---|---|---|---|
| 2,100,861 | 11/1937 | Lockhead | 66/198 |
| 3,983,870 | 10/1976 | Herbert et al. | 602/63 |
| 4,021,860 | 5/1977 | Swallow et al. | 2/239 |
| 4,149,274 | 4/1979 | Garrou et al. | 2/239 |
| 4,651,354 | 3/1987 | Petrey | 2/239 |
| 4,745,917 | 5/1988 | Harty et al. | 602/63 |

FOREIGN PATENT DOCUMENTS

| | | | |
|---|---|---|---|
| 2635001 | 2/1990 | France | 602/63 |
| 1428243 | 3/1976 | United Kingdom | 2/239 |
| 2111833 | 7/1983 | United Kingdom | 602/63 |
| 2246281 | 1/1992 | United Kingdom | 2/239 |

*Primary Examiner*—Robert A. Hafer
*Assistant Examiner*—Michael O'Neill
*Attorney, Agent, or Firm*—Alvin Isaacs

[57] ABSTRACT

A therapeutic stocking for applying compressive force to the wearer's leg having an integrally knit anti-slip feature on the foot portion. The anti-slip feature being knit of bare and covered elastomeric yarns. The anti-slip feature further having an instep portion and a sole portion having greater frictional characteristics than the instep portion. The sole portion being knit in a repeating pattern having courses of knit and float stitches of a covered elastomeric yarn and jersey courses of a bare elastomeric yarn. The bare elastomeric yarn being substantially on the exterior surface of the sole portion yielding a friction surface which is located to contact the floor beneath the wearer's foot and minimize slippage thereon.

11 Claims, 4 Drawing Sheets

5,412,957

KNIT THERAPEUTIC STOCKING WITH ANTI-SLIP FEATURE

BACKGROUND OF INVENTION

1. Field of invention

This invention relates to knit therapeutic compression stockings for use primarily by patients to apply compressive forces to their leg(s) to reduce to possibility of thromboemoblisms. More particularly, this invention relates to therapeutic knit stockings having frictional surfaces on the foot portion of the stocking to prevent slipping by the patient when walking on a floor.

2. Prior Art

Therapeutic or anti-embolism stockings are used to apply compressive force to the wearer's leg. This force is usually applied in the form of a pressure gradient which decreases progressively from the ankle to the upper thigh of the leg. Such stockings are designed to increase the velocity of the blood flowing through the leg thereby reducing the probability of thromboembolism. Therapeutic stockings have found general use in hospitals to reduce the chances of embolism in post-operative and bed-ridden patients. However, because the stockings are used in a hospital environment, there exists a tendency for them to be worn without other footwear. Because of this, there is an increased possibility that an ambulatory patient could slip on the smooth hospital floors. Therefore, anti-slip means have been developed to minimize the danger of a patient's slipping while wearing the stocking.

Prior art such as that in U.S. Pat. No. 4,021,860 issued to Swallow et al. provides an anti-slip feature by fusing a thermoplastic material to the bottom or foot of the stocking. However, because the anti-slip feature is not integrally knit into the stocking, an extra step is required in the manufacturing process to remove the stocking from the knitting machine and place it in an apparatus to fuse the thermoplastic material to foot of the stocking. This extra step increases the cost of manufacturing making it less economically desirable. Additionally, since the anti-slip feature was fused to the outer surface of the stocking, it is susceptible to delaminating after extensive use or repeated washings. More importantly, the thermoplastic material is relatively inelastic and when fused to the stocking it would impair the stretch characteristics of the stocking thereby limiting the ability of the stocking to function for the purpose for which it was primarily designed.

Subsequent prior art such as that in U.S. Pat. No. 4,149,274 issued to Garrou et al. recognized the limitations in affixing the anti-slip means to the outer surface of the stocking and provided an improved anti-slip means which was incorporated into the stocking during the knitting of the stocking. Garrou et al. describes an anti-slip means wherein friction yarns, such as an uncovered spandex, are interknit with the stocking's body yarn using tuck and float stitching. These stitches form unknit portions of friction yarn on the interior surface of the stocking during knitting. The stocking is then everted to expose these unknit portions of friction yarn which form the anti-slip means. These unknit friction yarns engage the floor to minimize slippage. However, as with the earlier prior art, an extra manufacturing step is required to expose the anti-slip means. Additionally, the unknit portions of friction yarn, while acting as an anti-slip means, can also increase the probability that the unknit yarns will snag on a rough surface resulting in either a damaged stocking or perhaps tripping the patient. Thus, although the prior art has been somewhat successful in providing an anti-slip feature for therapeutic stockings, there still exist significant disadvantages in the prior art. The present invention provides a distinct advantage over the prior art by using an integrally knit design which does not require the knit stocking to be everted nor does it leave unknit yarns on the exterior surface which could cause the stocking to snag.

SUMMARY OF THE INVENTION

The present invention provides an anti-slip feature which is knit from a covered elastomeric yarn and a friction yarn such as a bare elastomeric yarn. The anti-slip feature is integrally knit into the stocking while the stocking is being knitted and does not require the stocking to be everted to expose the friction surface. Thus, the present invention has succeeded where the prior art has failed in producing an integrally knit anti-slip feature without requiring additional manufacturing steps.

The anti-slip feature is knit into the foot portion of the stocking and is divided into instep and sole portions. The sole portion being knit in a repeating pattern having courses of knit and float stitches of a covered elastomeric yarn and jersey courses of a bare elastomeric yarn. The knitting pattern of the sole portion generates a friction surface on the exterior surface of the stocking and gives the sole portion greater frictional properties than the instep portion.

The object of the invention is to provide an integrally knit anti-slip feature to contact the floor beneath the wearer's foot to minimize slippage thereon.

Another object of this invention is to provide an anti-slip feature that is integrally knit within the stocking so as to eliminate the need to evert the stocking after it has been knit and removed from the knitting machine.

Another object is to provide an anti-slip feature which does not leave unknit loops of yarn on the exterior surface which could cause the stocking to snag and damage the stocking or trip the wearer.

A further object is to provide an anti-slip feature which does not inhibit the ability of the therapeutic stocking to apply compressive force to the patient's limb.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
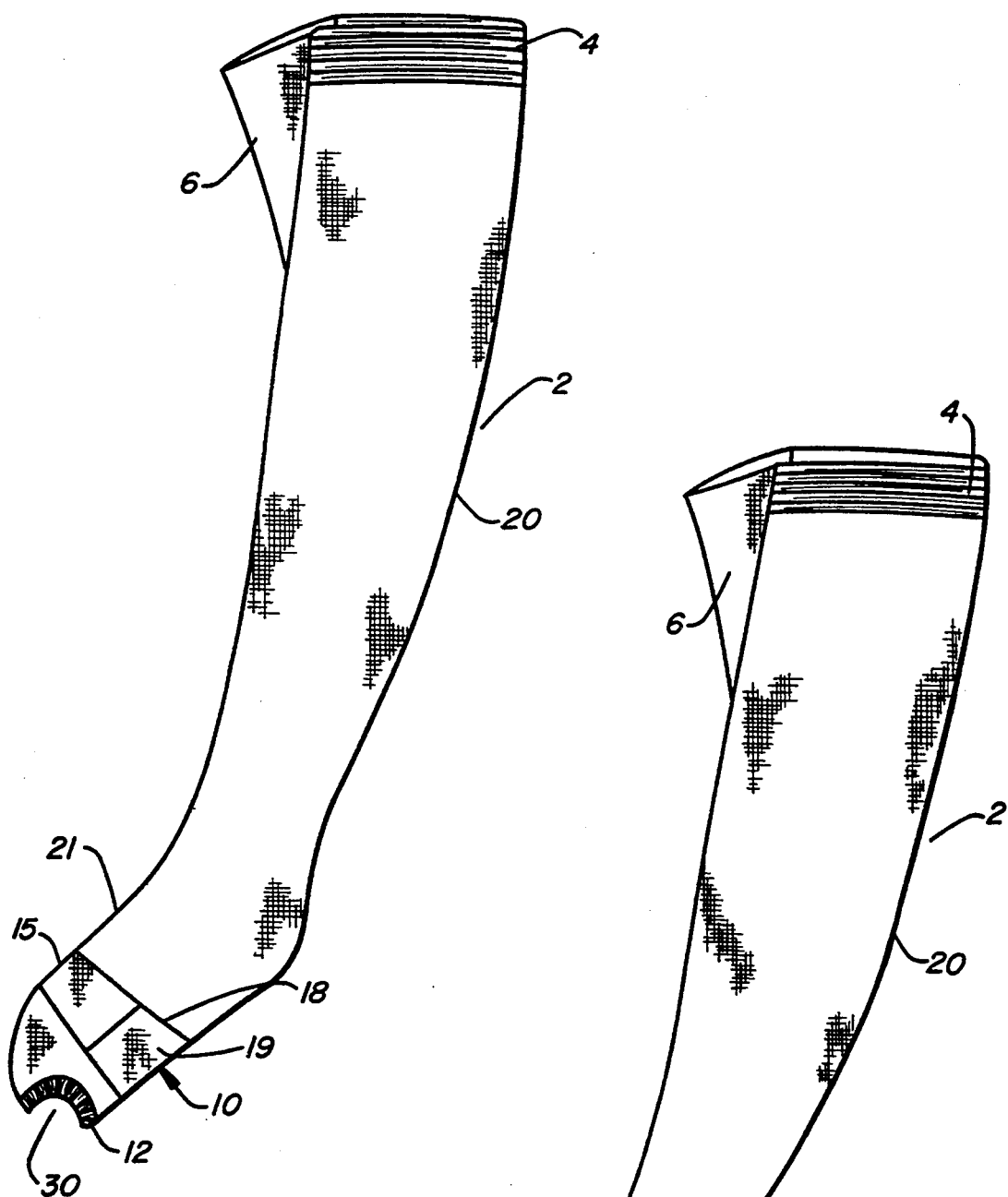
FIG. 1 is a side elevational view of the therapeutic stocking of the present invention.
Figure 2:
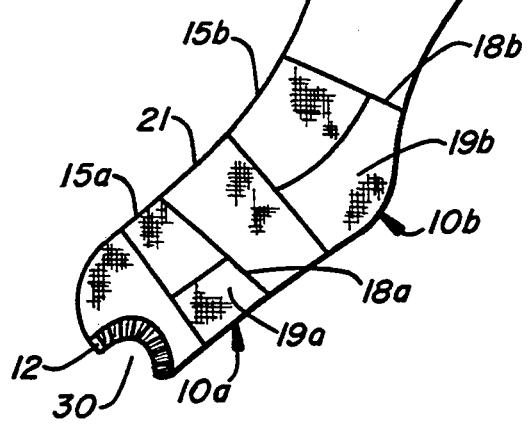
FIG. 2 is a side elevational view of the therapeutic stocking of the present invention in another embodiment.
Figure 3:
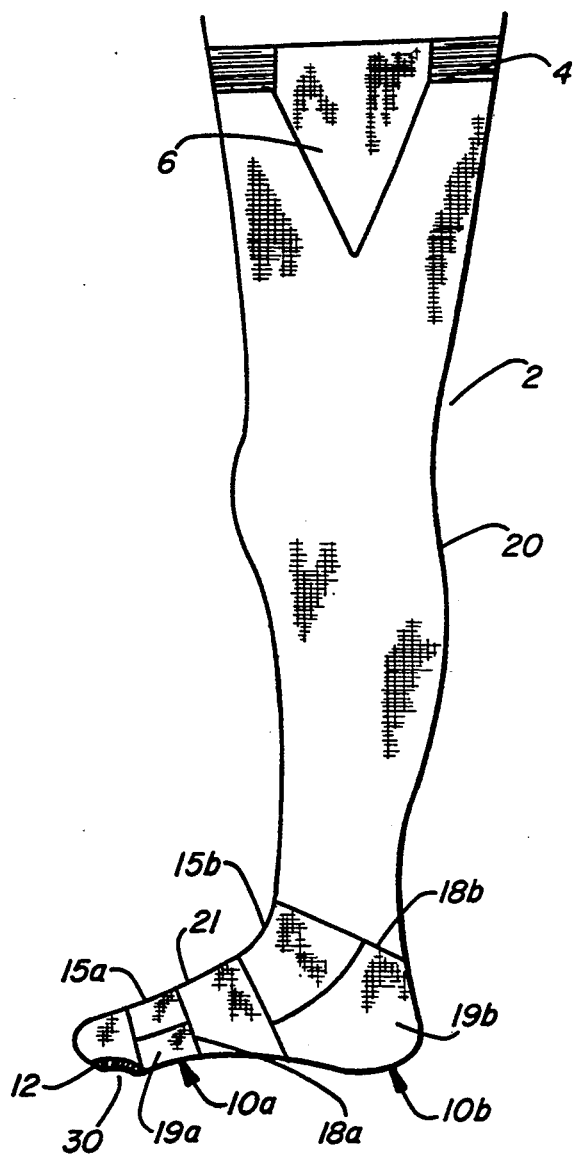
FIG. 3 is a side elevational view of the embodiment of FIG. 2 illustrating the positioning of the anti-slip features of the present invention with respect to the wearer's leg.

FIGS. 1-3 illustrate the therapeutic stocking of the present invention. Generally, the therapeutic stocking 2 has a leg portion 20 and a foot portion 21 which are both circumferentially elastic in order to apply a pressure gradient to the patient's leg. The pressure gradient normally used decreases in the direction from patient's foot to thigh. The leg portion 20 has an insert 6 in the inner upper thigh region and a partial elastic band 4 attached to the stockings upper end. The partial elastic band 4 extends only part way around the circumference of the leg portion 20 and is attached at either end to the insert 6. The insert 6 is placed so as not to constrict the blood flow through the deep and superficial blood vessel plexus in the patient's inner upper thigh. The stocking 2, with the exception of the anti-slip features, is knit in a conventional manner using a texturized stretchable nylon yarn and a covered elastomeric yarn. The texturized nylon yarn is preferably a 70-1-17 stretch nylon with one end texturized in the "S" direction and two end texturized in the "Z" direction. The covered elastomeric yarn is preferably 280 denier, type 126 DuPont LYCRA spandex covered with one end 70-1-34 stretch nylon manufactured by DuPont. The stocking is knit using a Matec Pois DME 4 hosiery knitting machine manufactured by Savio, Florence, Italy. Although, it is anticipated that other machines having similar knitting capabilities can be utilized.

Referring to FIG. 1, the foot portion 21 of this embodiment has a toe inspection port 30 which is defined by welt 12 and an anti-slip feature 10 which is integrally knit into the stocking. The anti-slip feature 10 has instep portion 15 and sole portion 18. The exterior surface 19 of sole portion 18 is a high friction surface which is positioned to contact the floor beneath the patient's foot and minimize slippage thereon.

FIG. 2 presents another embodiment of the present invention wherein the stocking construction is similar to that of FIG. 1 except that the foot portion 21 has two anti-slip features 10a and 10b having instep portions 15a and 15b and sole portions 18a and 18b. The exterior surfaces 19a and 19b of sole portions 18a and 18b are high friction surfaces. One of the sole portions 18a is positioned to contact the floor beneath the ball of the patient's foot. The other sole portion 18b is positioned to contact the floor beneath the heel of the patient's foot. FIG. 3 shows the stocking of FIG. 2 on the patient's leg.

Figure 4:
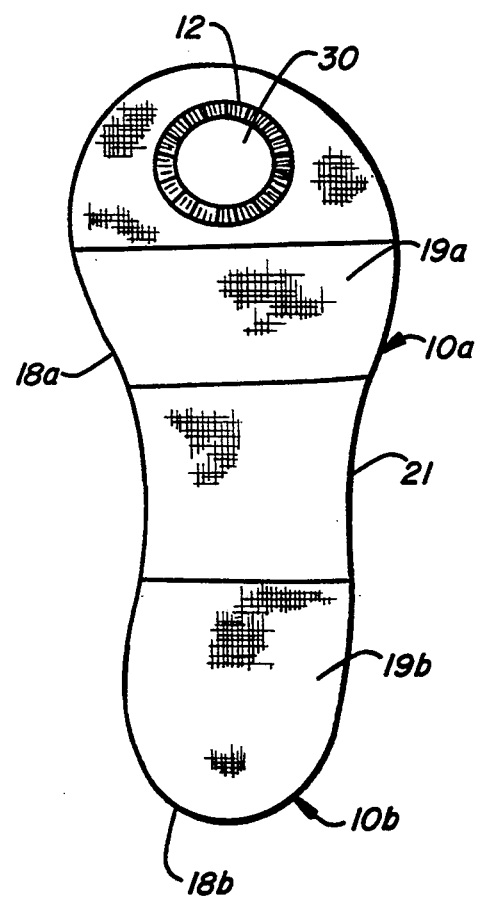
FIG. 4 is an greatly enlarged view of the underside of the foot portion of FIG. 3 showing the anti-slip features of the present invention.

The positioning of the sole portions 18a and 18b of FIGS. 2 and 3 is better illustrated in FIG. 4. The exterior surfaces 19a and 19b of sole portions 18a and 18b present high friction surfaces which extend laterally across the width of the patient's foot. The sole portion 18a is positioned in the ball region of the patient's foot and adjacent to the toe inspection port 30 which is defined by circular welt 12. The sole portion 18b is in the heel region of the patient's foot and completely covers the heel. The embodiment illustrated in FIG. 2 is preferred because it presents the greatest area of friction surface by having two anti-slip features. However, the embodiment of FIG. 1 is more economical to manufacture because it has only one anti-slip feature.

Figure 5:
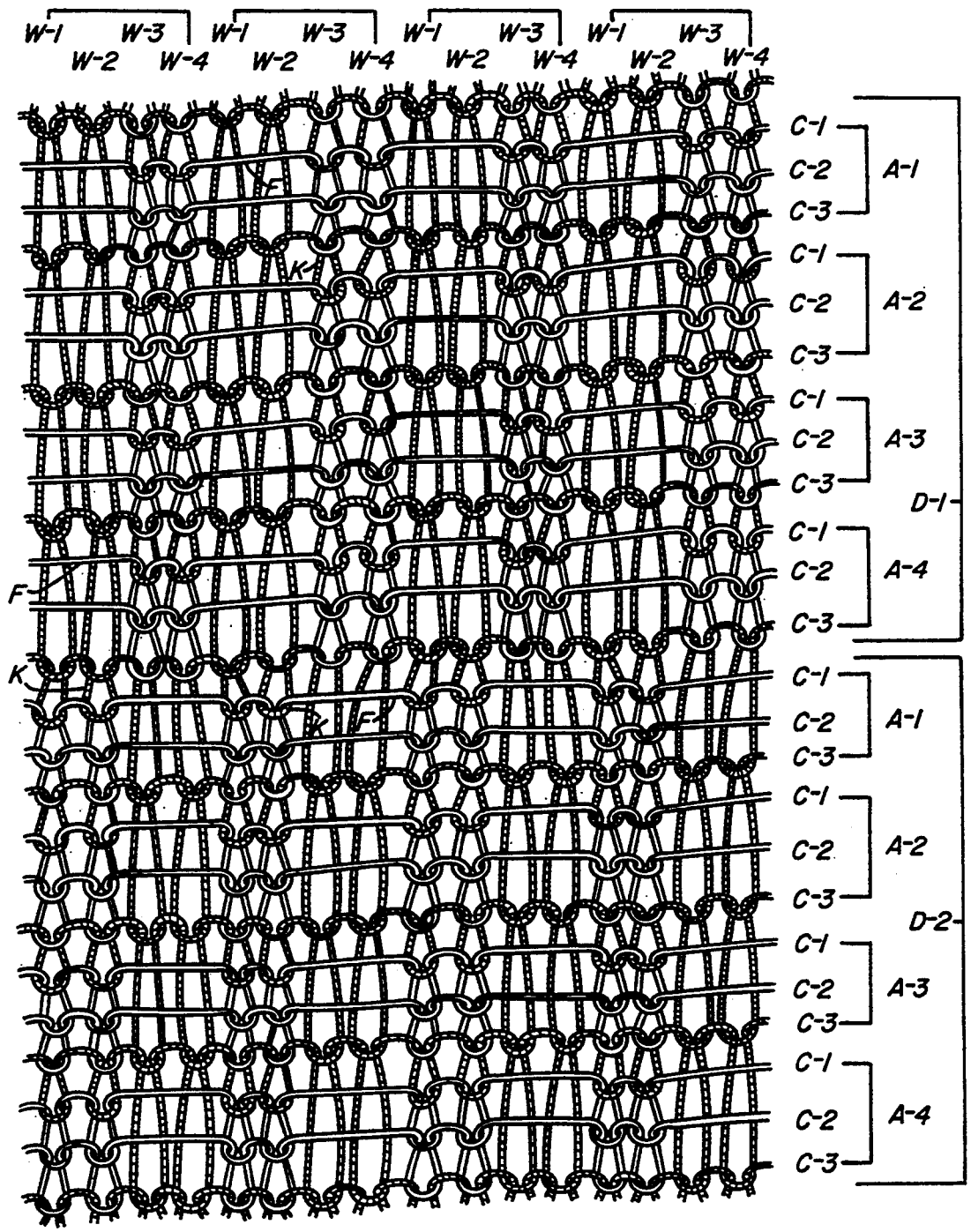
FIG. 5 is a greatly enlarged partial view of the sole portion of the anti-slip feature of the present invention showing its knit construction.

Referring to FIG. 5, the sole portions 18, 18a and 18b of the anti-slip features 10, 10a and 10b of FIGS. 1-4 are knit in a repeating twenty-four course, four wale pattern. The twenty-four course, four wale pattern shown in FIG. 5 includes alternate twelve course patterns, D-1 and D-2 each having four repetitions of a three course pattern, A-1, A-2, A-3 and A-4. Each three course pattern having two adjacent courses C-1 and C-2 of straight selection knit, K, and float, F, stitches in a 2:2 selection (i.e. two consecutive knit stitches followed by two consecutive float stitches) of a covered elastomeric yarn followed by a jersey course C-3 of a bare elastomeric yarn (the bare elastomeric yarn is striped for the purpose of clarity). The first two wales, W-1 and W-2, contain the float stitches F of the first twelve course pattern D-1 and the knit stitches K of the second twelve course pattern D-2. The second two wales, W-3 and W-4, contain the knit stitches K of the first twelve course pattern D-1 and the float stitches F of the second twelve course pattern D-2. The two twelve course patterns D-1 and D-2 are alternated such they are staggered walewise.

The bare elastomeric yarn of the jersey course C-3 is substantially on the exterior surface of the stocking, as knit, and the loose float stitches F are on the interior surface of the stocking. Thus, the stocking need not be everted to expose the friction surfaces of the anti-slip features.

Figure 6:
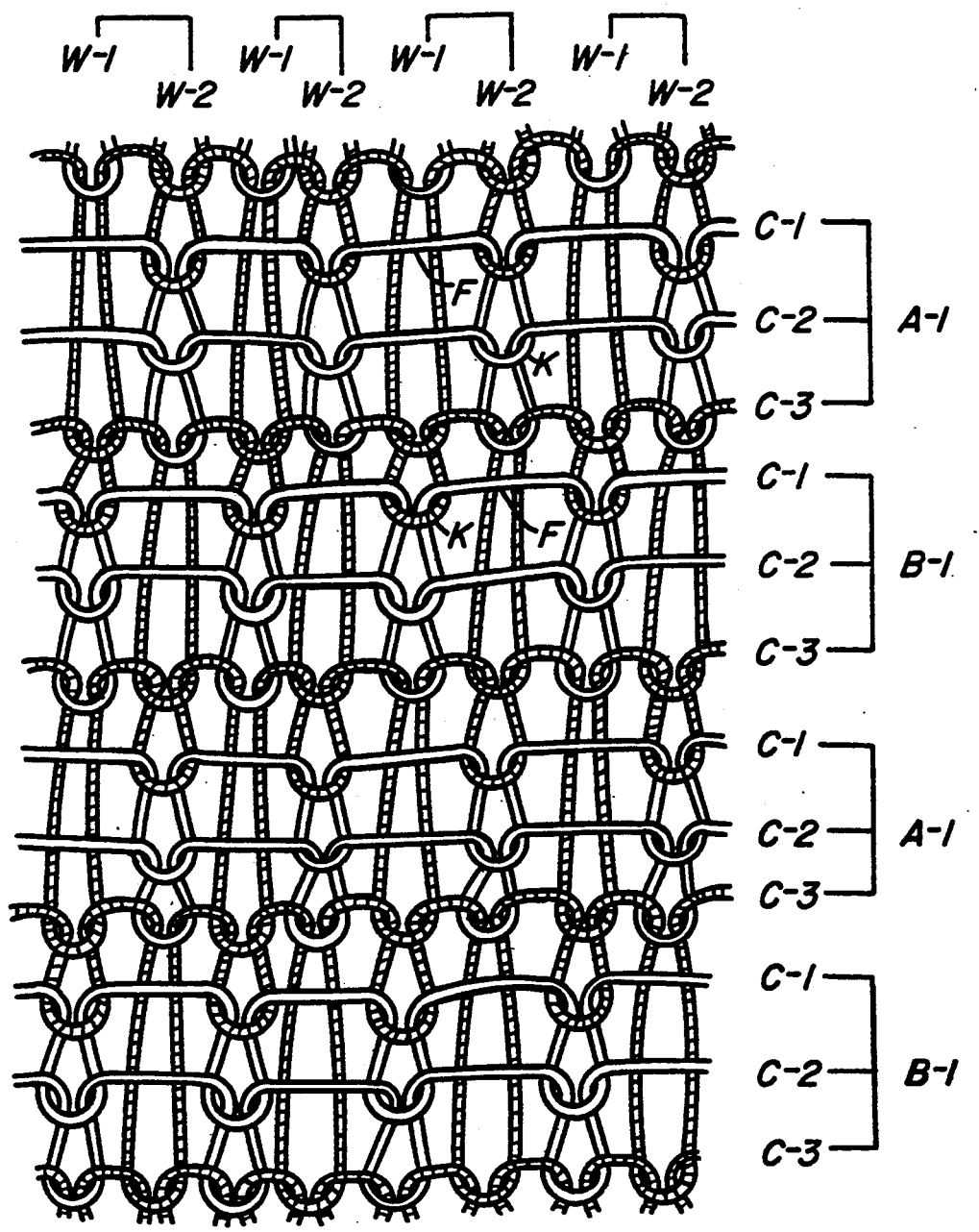
FIG. 6 is a greatly enlarged partial view of the instep portion of the anti-slip feature of the present invention showing its knit construction.

Referring to FIG. 6, the instep portions 15, 15a and 15b of the anti-slip features 10, 10a and 10b of FIGS. 1-4 are knit in a repeating six course, two wale pattern having first, second, fourth and fifth courses of alternating knit and float stitches of a covered elastomeric yarn and third and sixth jersey courses of a bare elastomeric yarn. The knit stitches of the first and second courses and the float stitches of the fourth and fifth courses being in one wale, the float stitches of the first and second courses and the knit stitches of the fourth and fifth courses being in the other wale. The six course, two wale pattern shown in FIG. 6 includes alternate three course patterns A-1 and B-1. Each three course pattern having two courses C-1 and C-2 of straight selection knit, K, and float, F, stitches in a 1:1 selection (i.e. alternating single knit and float stitches) of a covered elastomeric yarn followed by a jersey course C-3 of a bare elastomeric yarn (the bare elastomeric yarn is striped for clarity). The wale W-1 contains the float stitches F of the three course pattern A-1 and the knit stitches K of the three course pattern B-1. The wale W-2 contains the knit stitches K of the three course pattern A-1 and the float stitches F of the three course pattern B-1. Such that the two three course patterns A-1 and B-1 are staggered walewise.

The bare elastomeric yarn of the instep and sole portions of the anti-slip features is preferably a 240 denier spandex such as Globe's CLEARSPAN Spandex manufactured by Globe Manufacturing Inc., Fall River, Mass. The covered elastomeric yarn of the instep and sole portions of the anti-slip features is preferably 70 denier, type 146 DuPont LYCRA spandex covered with two end 20-1-7 flat nylon, type 280. Other friction yarns could also be used provided that they do not interfere with the elasticity of the stocking and its ability to apply compressive forces to the patient's limb.

While several embodiments have been described, it is apparent that other variations may be made without departing from the scope of the invention set forth in the appended claims.

What is claimed is:

1. A therapeutic stocking for covering a patient's leg and foot having circumferentially elastic leg and foot portions, the toot portion having an anti-slip feature comprising:
- an instep portion having elastomeric yarns knit in a repeating pattern;
- a sole portion having an exterior surface and being knit in a repeating pattern having courses of knit and float stitches of a covered elastomeric yarn and jersey courses of a bare elastomeric yarn, the bare elastomeric yarn being substantially on the exterior surface of the knitted sole portion, the sole portion being located to contact the exterior surface of the sole portion with a floor beneath the patient's foot to minimize slippage of the patient's foot on the floor;
- the repeating pattern of tile instep portion being a six course, two wale pattern having first, second, fourth and fifth courses of alternating knit and float stitches of a covered elastomeric yarn and third and sixth jersey courses of a bare elastomeric yarn, the knit stitches of the first and second courses and the float stitches of the fourth and fifth courses being in one wale, the float stitches of the first and second courses and the knit stitches of the fourth and fifth courses being in the other wale; and
- the repeating pattern of the sole portion being a twenty-four course, four wale pattern including two alternating twelve course patterns having four repetitions of a three course pattern having two adjacent courses of knit and float stitches of a covered elastomeric yarn in a 2:2 selection followed by a jersey course of a bare elastomeric yarn, the float stitches of the first twelve course pattern and the knit stitches of the second twelve course pattern being in the first and second wales and, the knit stitches of the first twelve course pattern and the float stitches of the second twelve course pattern being in the third and fourth wales.

2. The therapeutic stocking of claim 1 wherein the sole portion of the anti-slip feature is located contact the floor beneath the ball of the patient's foot.

3. The therapeutic stocking of claim 2 further comprising a second anti-slip feature having a sole portion located to contact the floor beneath the heel of the patient's foot.

4. The therapeutic stocking of claim 1 wherein the covered elastomeric yarn is nylon covered spandex yarn.

5. The therapeutic stocking of claim 1 wherein the bare elastomeric yarn is a bare spandex yarn.

6. A therapeutic stocking for covering a patient's leg and foot having circumferentially elastic leg and foot portions, tile foot portion having an anti-slip feature comprising:
- an instep portion having elastomeric yarns knit in a repeating pattern;
- a sole portion-having an exterior surface and being knit in a repeating pattern having courses of knit and float stitches of a covered elastomeric yarn and jersey courses of a bare elastomeric yarn;
- the repeating pattern of the sole portion being a twenty-four course, four wale pattern including two alternating twelve course patterns having four repetitions of a three course pattern having two adjacent courses of knit and float stitches of a covered elastomeric yarn in a 2:2 selection followed by a jersey course of a bare elastomeric yarn, the float stitches of the first twelve course pattern and the knit stitches of the second twelve course pattern being in the first and second wales and, the knit stitches of the first twelve course pattern and the float stitches of tile second twelve course pattern being in the third and fourth wales;
- the bare elastomeric yarn being substantially on the exterior surface of the sole portion as knit;
- the sole portion being located to contact the exterior surface of the sole portion with a floor beneath the patient's foot to minimize slippage of the patient's foot on the floor;
- the repeating pattern of the instep portion being a six course, two wale pattern having first, second, fourth and fifth courses of alternating knit and float stitches of a covered elastomeric yarn and third and sixth jersey courses of a bare elastomeric yarn, the knit stitches of the first and second courses and tile flat stitches of the fourth and fifth courses being in one wale, the float stitches of the first and second courses and the knit stitches of the fourth and fifth courses being in the other wale.

7. The therapeutic stocking of claim 6 wherein the sole portion of the anti-slip feature is located to contact the floor beneath the ball of the patient's foot.

8. The therapeutic stocking of claim 7 further comprising a second anti-slip feature having a sole portion located to contact the floor beneath the heel of the patient's foot.

9. The therapeutic stocking of claim 6 wherein the covered elastomeric yarn is nylon covered spandex yarn.

10. The therapeutic stocking of claim 6 wherein the bare elastomeric yarn is a bare spandex yarn.

11. The therapeutic stocking of claim 6 wherein the sole portion has a higher coefficient of friction than the instep portion.

* * * * *